US011229626B2

(12) United States Patent
Samant et al.

(10) Patent No.: US 11,229,626 B2
(45) Date of Patent: Jan. 25, 2022

(54) SYNERGISTIC NUTRITIONAL COMPOSITIONS FOR TREATING SEIZURES AND CHRONIC INFLAMMATORY DISEASES

(71) Applicant: CELAGENEX RESEARCH (INDIA) PVT. LTD., Maharashtra (IN)

(72) Inventors: Rajaram Samant, Thane-West (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/330,297

(22) Filed: May 25, 2021

(65) Prior Publication Data
US 2021/0369676 A1  Dec. 2, 2021

(30) Foreign Application Priority Data
May 26, 2020 (IN) .............................. 202021021984

(51) Int. Cl.
| A61K 31/4172 | (2006.01) |
| A61K 31/23 | (2006.01) |
| A61P 25/08 | (2006.01) |
| A61K 31/145 | (2006.01) |
| A61K 31/4045 | (2006.01) |
| A61K 9/00 | (2006.01) |

(52) U.S. Cl.
CPC ........ *A61K 31/4172* (2013.01); *A61K 9/0053* (2013.01); *A61K 31/145* (2013.01); *A61K 31/23* (2013.01); *A61K 31/4045* (2013.01); *A61P 25/08* (2018.01)

(58) Field of Classification Search
CPC .. A61K 31/4172; A61K 31/145; A61K 31/23; A61K 31/4045; A61K 9/0053; A61P 25/08
See application file for complete search history.

(56) References Cited

U.S. PATENT DOCUMENTS

| 9,737,525 B2 | 8/2017 | Kazantsev et al. | |
| 2007/0244175 A1* | 10/2007 | Beelman ................. | A61P 25/28 514/401 |
| 2016/0199337 A1* | 7/2016 | Morris .................... | A23L 33/12 424/93.4 |

FOREIGN PATENT DOCUMENTS

| EP | 1764361 B1 | 1/2013 |
| EP | 3573968 A1 | 12/2019 |
| EP | 3644985 A1 | 5/2020 |
| WO | 2018/189113 A1 | 10/2018 |

OTHER PUBLICATIONS

Casillas-Espinosa et al., "Regulators of synaptic transmission: roles in the pathogenesis and treatment of epilepsy", Molecular Plasticity, Epilepsia. Dec. 7, 2012; 53 Suppl 9:41-58.
Tanaka et al., "The evolutionarily conserved porcupine gene family is involved in the processing of the Wnt family." Jul. 2000, Europ. J. Biochem. 267(13): 4300-4311.
Krestel et al. "A Genetic Switch for Epilepsy in Adult Mice", The Journal of Neuroscience : The Official Journal of the Society for Neuroscience 24(46):10568-78, (Nov. 17, 2004).
Zhang, S., Zhu, Y., Cheng, J., & Tao, J., "Ion Channels in Epilepsy: Blasting Fuse for Neuronal Hyperexcitability", Epilepsy, (Jan. 2019).
Satlin et al., "Development of perampanel in epilepsy", Acta Neurologica Scandinavica 127(s197) Apr. 2013.
Chang et al., "The antiepileptic drug valproic acid and other medium-chain fatty acids acutely reduce phosphoinositide levels independently of inositol in Dictyostelium:", Dis Model Mech. Jan. 2012; 5(1):115-24.
Chang et al., "Seizure control by decanoic acid through direct AMPA receptor inhibition", Brain. Feb. 2016; 139(2): 431-443.
Enderlin et al., "Absence of increased blood decanoic acid levels in children with epilepsy treated with classic ketogenic diet", Epileptic Disorders, The Education Journal of the ILAE (International League Against Epilepsy), Aug. 2019; 21 (4): 366-9.
Lv et al., "Enhancement of Sodium Caprate on Intestine Absorption and Antidiabetic Action of Berberine", AAPS PharmSciTech. Mar. 2010; 11(1): 372-382.
Tan et al., "Tridecanoin is anticonvulsant, antioxidant, and improves mitochondrial function", J Cereb Blood Flow Metab. Jun. 2017; 37(6): 2035-2048.
Wang et al., "Activation of Nrf2-ARE signal pathway protects the brain from damage induced by epileptic seizure", Brain Res. Jan. 28, 2014; 1544:54-61.

(Continued)

*Primary Examiner* — Kara R McMillian
(74) *Attorney, Agent, or Firm* — Maschoff Brennan

(57) ABSTRACT

The invention disclosed herein relates to novel synergistic nutritional compositions for treating seizures and chronic inflammatory diseases. Particularly, the invention relates to potent and stable synergistic nutritional composition comprising combination of therapeutically active non-competitive amino-3-hydroxy-5-methyl-4-isoxazolepropionic acid (AMPAR) antagonists and nuclear factor erythroid 2-related factor 2 (NRF2) activators, present in weight ratio of 1:0.001 to 1:0.5, along with pharmaceutically acceptable excipients. Further, the present synergistic nutritional composition is useful for treating conditions associated with seizure, fibrosis and diabetes.

6 Claims, 2 Drawing Sheets

(56) References Cited

OTHER PUBLICATIONS

Egea et al., "Melatonin-sulforaphane hybrid ITH12674 induces neuroprotection in oxidative stress conditions by a 'drug-prodrug' mechanism of action", Journal List Br J Pharmacol. Apr. 2015; 172(7): 1807-1821.
Socala et al., "Increased seizure susceptibility and other toxicity symptoms following acute sulforaphane treatment in mice", Toxicol Appl Pharmacol. Jul. 2017, 1; 326:43-53.

* cited by examiner

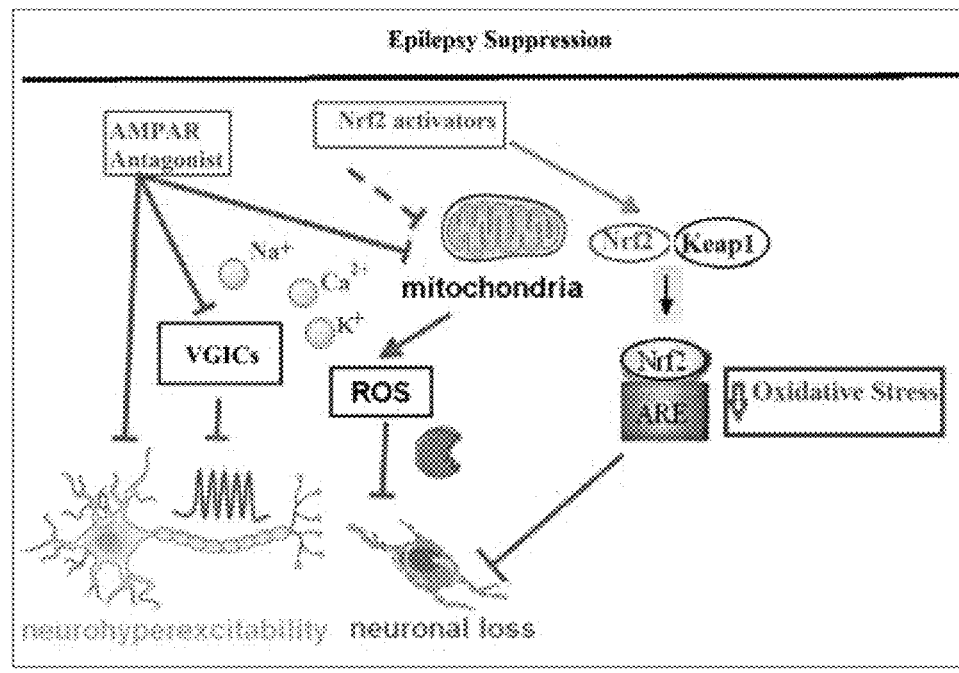
Figure 1: Epilepsy Suppression
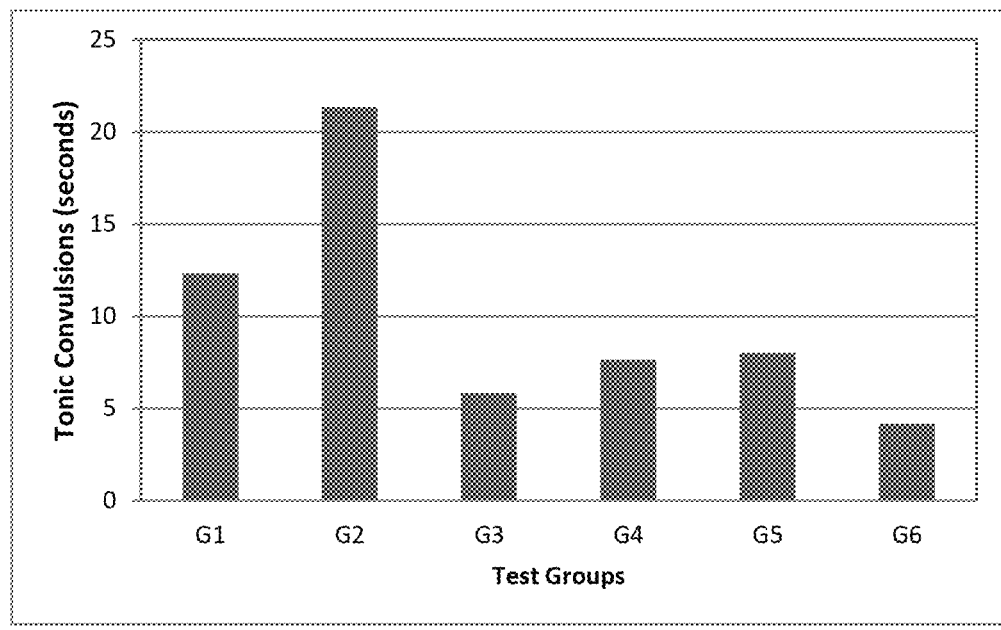
Figure 2: Test Groups vs. Tonic Convulsions

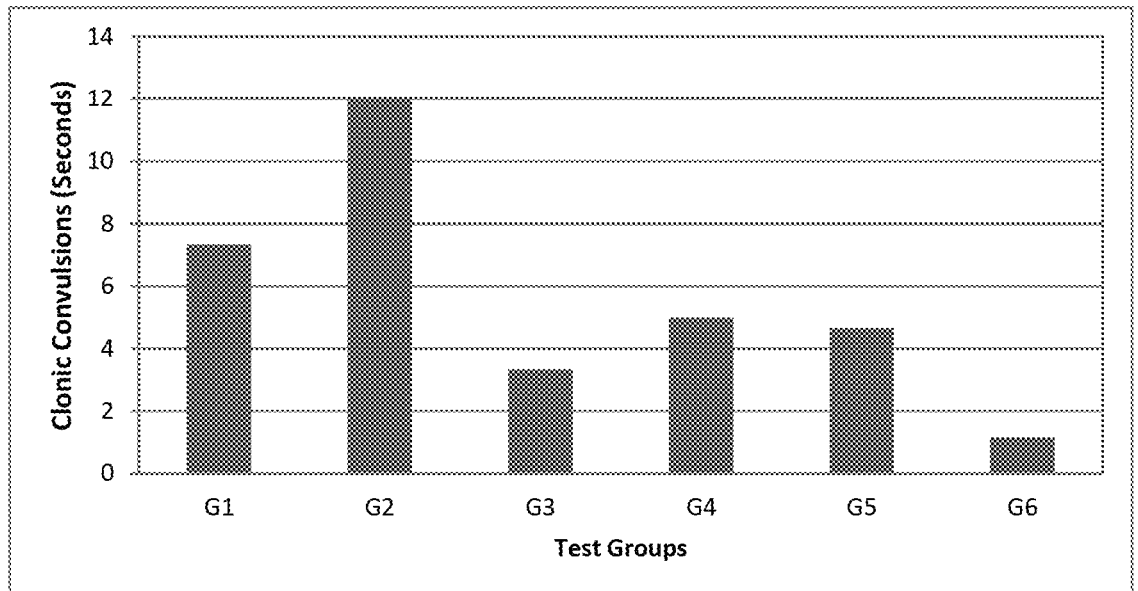
Figure 3: Test Groups vs. Clonic Convulsions
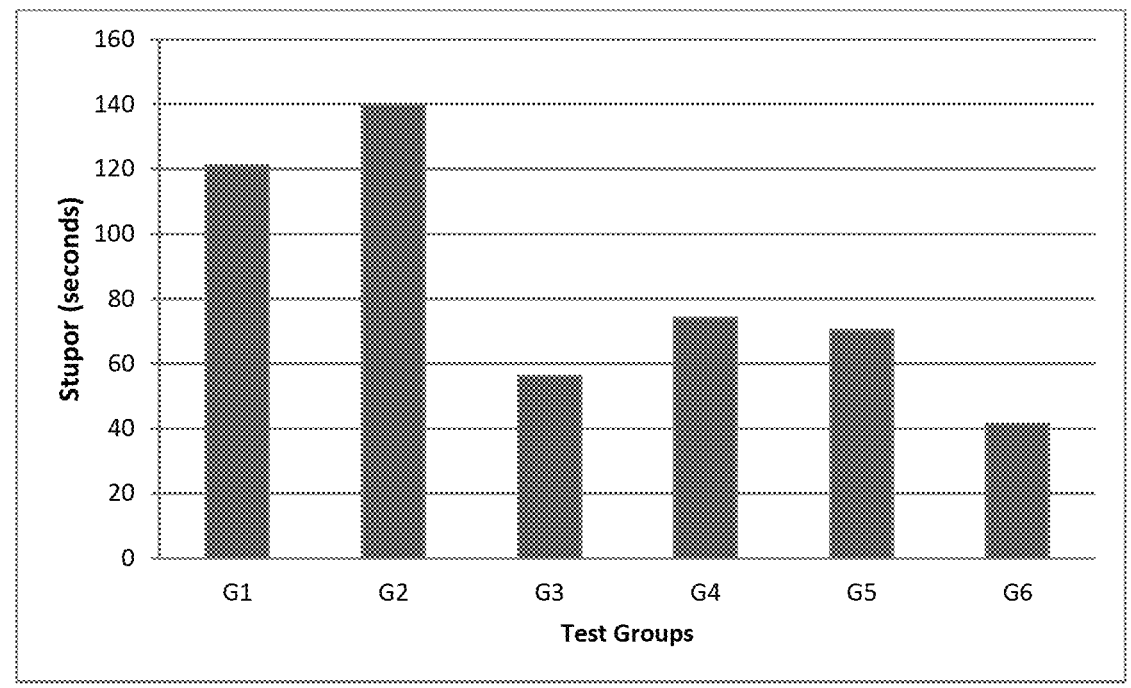
Figure 4: Test Groups vs. Stupor

SYNERGISTIC NUTRITIONAL COMPOSITIONS FOR TREATING SEIZURES AND CHRONIC INFLAMMATORY DISEASES

FIELD OF THE INVENTION

The present invention discloses novel synergistic nutritional compositions for treating seizures and chronic inflammatory diseases. Particularly, the invention relates to potent synergistic nutritional composition comprising exogenous combination of α-amino-3-hydroxy-5-methyl-4-isoxazole-propionic acid receptor (AMPAR) antagonists and nuclear factor erythroid 2-related factor 2 (NRF2) activators present in suitable weight ratio, along with pharmaceutically acceptable recipients. More particularly, the invention provides potent synergistic nutritional composition comprising exogenous combination of tridecanoin and L-ergothioneine present in suitable weight ratio, along with pharmaceutically acceptable recipients.

BACKGROUND OF THE INVENTION

Seizure disorder relates to any condition in which seizures may be a symptom. Seizure disorder is often used in place of the term "epilepsy". A general definition for the word "seizure" is a period of abnormal, synchronous excitation of a neuronal population. Seizures typically last for seconds or minutes but can be prolonged and continuous in the case of status epilepticus. A seizure refers to a single surge of electrical activity in a person's brain. A seizure disorder is a condition in which a person has multiple seizures. The tendency to have recurrent seizures leads to epilepsy. Moreover, epilepsy is a neurological condition characterized by two or more unprovoked seizures.

Anything that interrupts the normal connections between nerve cells in the brain can cause a seizure. This includes a high fever, low blood sugar, high blood sugar, alcohol or drug withdrawal, or a brain concussion. Under these circumstances, anyone can have one or more seizures. However, when a person has two or more recurrent, unprovoked seizures, he or she is considered to have epilepsy. There are many possible causes of epilepsy, including an imbalance of nerve-signaling chemicals called neurotransmitters, tumors, strokes, and brain damage from illness or injury, or some combination of these.

A seizure occurs when part(s) of the brain receives a burst of abnormal electrical signals that temporarily interrupts normal electrical brain function. It is a sudden, uncontrolled electrical disturbance in the brain. It can cause changes in human behavior, movements or feelings, and in levels of consciousness.

The type of seizure depends on which part of the brain and how much of the brain is affected and what happens during the seizure. The two broad categories of epileptic seizures are generalized (absence, atonic, tonic-clonic, myoclonic) seizures and partial (simple and complex) seizures.

The term "seizure" is often used interchangeably with "convulsion". During convulsions a person has uncontrollable shaking that is rapid and rhythmic, with the muscles contracting and relaxing repeatedly. A seizure, formally known as an epileptic seizure, is a period of symptoms due to abnormally excessive or contemporaneous neuronal activity in the brain. Most of the time these episodes last less than 2 minutes and it takes some time to return to normal.

A profusion of new antiepileptic drugs (AEDs) has appeared in the past 5 years. It is further needed to understand how normal neuronal function goes awry in epilepsy, particularly normal synaptic transmission and neuronal firing, and the mechanisms by which AEDs control the hyperexcitability that underlies epilepsy.

According to the World Health Organization report, epilepsy accounts for a significant proportion of the world's disease burden, affecting around 50 million people worldwide. The estimated proportion of the general population with active epilepsy (i.e., continuing seizures or with the need for treatment) at a given time is between 4 and 10 per 1000 people. Globally, an estimated five million people are diagnosed with epilepsy each year. In high-income countries, there are estimated to be 49 per 100,000 people diagnosed with epilepsy each year. In low- and middle-income countries, this figure can be as high as 139 per 100,000 people. Nearly 80% of people with epilepsy live in low- and middle-income countries. Almost 3 million Americans live with epilepsy.

Epilepsy is not contagious. Although many underlying disease mechanisms can lead to epilepsy, the cause of the disease is still unknown in about 50% of the cases globally. The causes of epilepsy are divided into the following categories: structural, genetic, infectious, metabolic, immune, which include brain damage from prenatal or perinatal; congenital abnormalities or genetic conditions with associated brain malformations; severe head injury; ischemic stroke; an infection of the brain such as meningitis, encephalitis or neurocysticercosis, certain genetic syndromes; and a brain tumour.

Genetic mutations may play a key role in the development of certain epilepsies. Many types of epilepsy affect multiple blood-related family members, directing to a strong inherited genetic component. In other cases, gene mutations may occur spontaneously and contribute to development of epilepsy in people with no family history of the disorder (called "de novo" mutations). Overall, researchers estimate that hundreds of genes could play a role in the seizure disorders.

The American Association of Neurological Surgeons have reported that epilepsy affects more than 300,000 children under the age of 15, and more than 90,000 young people in this group have seizures that cannot be adequately treated. The onset rate starts to increase when individuals age, particularly as they develop strokes, brain tumors or Alzheimer's disease, all of which may cause epilepsy. Reports indicate that more than 570,000 adults over the age of 65 suffer from the disorder.

Epilepsy, a disorder that affects 1% of the population worldwide, is classically thought to arise from an imbalance between excitation and inhibition in a localized region, multiple brain areas or the whole brain. Long-term changes in presynaptic morphology and synaptic vesicle recycling have been described in the animal models of epilepsy. These changes include alterations in the morphology of mossy fiber synaptic buttons, including increased size, number of release sites, and number of vesicles in the reserve pool and the readily releasable pool.

Synaptic transmission is regulated by diverse mechanisms, including presynaptic modulators of synaptic vesicle formation and release, postsynaptic receptors and signaling, and modulators of neurotransmission. Neurotransmitters released presynaptically can bind to their postsynaptic receptors, the inhibitory γ-aminobutyric acid (GABA)ergic receptors or the excitatory glutamate receptors. Once released, glutamate activates a variety of postsynaptic receptors including α-amino-3-hydroxy-5-methyl-4-isoxazole-propionic acid (AMPA), N-methyl-D-aspartate (NMDA), kainate, and metabotropic receptors. The activation of the receptors triggers downstream signaling cascades generating a vast array of effects, which can be modulated by numerous auxiliary regulatory subunits. Abnormalities in the regulation of synaptic transmission play a critical role in the pathogenesis of numerous brain diseases, including epilepsy. Therefore, it is important to identify the mechanisms involved in the regulation of synaptic transmission, which may serve as an essential component in the pathogenesis of epilepsy [*Epilepsia*. 2012 December; 53 *Suppl* 9:41-58].

Regulators of postsynaptic neurotransmission ionotropic glutamate receptors (α-amino-3-hydroxy-5-methyl-4-isoxazolepropionic acid [AMPA], N-methyl-D-aspartate [NMDA], play vital role in the regulation of synaptic transmission and thereby reduce the progression of epileptic seizures. The imbalance between AMPA receptors and calcium permeable AMPA receptors has been related to epileptogenesis [Tanaka et al., 2000].

Krestel et al. (2004) has showed that AMPA types of receptors enact a greater role in circuit hyperexcitability. The basic mechanism of neuronal excitability is the action potential, a hyperexcitable state can result from increased excitatory synaptic neurotransmission, decreased inhibitory neurotransmission, an alteration in voltage-gated ion channels, or an alteration of intra- or extra-cellular ion concentrations in favor of membrane depolarization.

Voltage-gated ions channels (VGICs), extensively distributed in the central nervous system (CNS), are responsible for the generation as well as modulation of neuroexcitability and considered as vital players in the pathogenesis of human epilepsy, by regulating the shape and duration of action potentials (APs). Particularly, genetic alterations or abnormal expression of voltage-gated sodium channels, voltage-gated potassium channels, and voltage-gated calcium channels are proved to be associated with epileptogenesis. The dysfunctional VGICs are like the blasting fuse for neuronal hyperexcitability and high-frequency neuron firing. Novel VGIC modulators are potentially an effective strategy for the development of novel antiepileptic drugs. Individualized precise treatment using matching VGIC drugs will provide novel research directions and antiepileptic strategies [Zhang, S., Zhu, Y, Cheng, J, & Tao, J. (2019). *Ion Channels in Epilepsy*].

As is the case throughout the central nervous system, fast synaptic excitation within and between brain regions relevant to epilepsy is mediated predominantly by AMPA receptors. By inhibiting neuronal excitability, AMPA receptor antagonists markedly reduce or abolish epileptiform activity and confer seizure protection in a subject.

NMDA receptors may also contribute to epileptiform activity, but NMDA receptor blockade is not sufficient to eliminate epileptiform discharges. AMPA receptors move into and out of the synapse in a dynamic fashion in forms of synaptic plasticity, underlying learning, and memory. Often, the trigger for these dynamic movements is the activation of NMDA receptors. While NMDA receptor antagonists inhibit these forms of synaptic plasticity, AMPA receptor antagonists do not impair synaptic plasticity and do not inhibit memory formation or retrieval [*Acta Neurologica Scandinavica* 127(s197) April 2013].

Also, it is observed that NMDA receptor antagonists sometimes induce "psychotomimetic" side effects, symptoms resembling psychosis. Such side effects caused by NMDA receptor inhibitors include hallucinations, paranoid delusions, confusion, difficulty concentrating, agitation, alterations in mood, nightmares, catatonia, ataxia, anaesthesia, and learning and memory deficits. Because of these psychotomimetic effects, NMDA receptor antagonists, especially phencyclidine, ketamine, and dextromethorphan, are used as recreational drugs.

Further NMDA antagonists are supposed to cause neurotoxicity in humans in the form of Olney's lesions, also known as NMDA receptor antagonist neurotoxicity (NAN). It is a form of potential brain damage due to drugs that have been studied experimentally and have produced neuronal damage.

In view of the physiological constraints associated with NMDA receptor inhibitors or antagonist, its use in the treatment of epilepsy is possibly less effective.

On the other hand, the inventors of present invention have found that active, non-competitive AMPA receptor antagonists are potential candidates for reducing progression of epilepsy.

Interestingly, the perampanel, a high-potency, orally active non-competitive AMPA receptor antagonist, supports the concept that AMPARs are critical to epileptic synchronization and the generation and spread of epileptic discharges in human epilepsy.

Further, EP Patent No. 1764361B1 discloses three anhydrous crystalline forms of perampanel and process for preparation thereof. However, perampanel has found to be less effective in certain types of seizures.

Therefore, the need arises to find out effective molecules that modulate AMPA receptors or inhibit AMPA receptor activity, that have potential to reduce excessive excitatory responses and may be promising future antiepileptic drugs (AEDs), with no adverse effects.

Although adverse effects can occur with all AEDs, among them CNS effects are the most prevalent ones. The failure of an AED regimen may be the result of unacceptable adverse effects (intolerance), inadequate seizure control (inefficacy) or a combination of both.

Further, literature has suggested that levetiracetam leads to behavioral side-effects such as aggression, hostility and nervousness in children with epilepsy compared to children who do not use levetiracetam.

Mood disorders, notably anxiety and depression, are common comorbidities in epilepsy that may be associated with AED therapy. Overall, adverse effects are a major reason for AED discontinuation. The future of epilepsy treatment awaits a "clean" AED that truly does not cause adverse effects in most patients. Further antiepileptic drugs are often insufficient to obtain seizure control and non-pharmacological interventions are often required. Currently available medications simply suppress seizure symptomatically, but do not appear to prevent seizure-induced brain injury or reverse the underlying mechanisms of epileptogenesis. Thus, it is now widely recognized that novel therapies for epilepsy need to be developed that have neuroprotective and antiepileptogenic properties.

In recent days, diet therapy is utilized in some patients with specific forms of epilepsy. Dietary therapies can provide control of seizures in patients with drug refractory epilepsy. There are several types of dietary therapies, all of which are high in fat, restrict carbohydrates to some extent, and are associated with ketosis. In the classical ketogenic diet introduced into clinical practice in the 1920s, the fat component is provided by long-chain triglycerides (LCTs). The medium-chain triglycerides (MCT) diet can be effective in seizure management and enhanced dietary intake of saturated fatty acid may provide additional therapeutic benefit.

The MCTs are mixed triglycerides of saturated fatty acids with a chain length of 6 to 12 carbon atoms, mainly C8

(caprylic acid) and C10 (capric acid). MCT oil can be obtained by direct or molecular distillation of virgin coconut oil. Particularly, MCT oils find many applications in cosmetics. It functions as a skin conditioning agent—occlusive as it slows the loss of water from the skin by forming a barrier on the skin's surface. It alters the thickness of liquid products and acts as a viscosity controlling agent.

The advance studies in recent days ensure that, treatment of adults with drug-resistant epilepsy, who show poor compliance to the stringent dietary regimen necessary for the MCT diet, may better tolerate a normal diet with just added fatty acid with C-10 carbon chain called decanoic acid, e.g., in the form of a triglyceride. Despite the long chain, the MCTs are more ketogenic than the LCTs.

The MCT ketogenic diet is widely considered to function by the generation of ketones, in the treatment of a range of disorders including epilepsy, cancer, Alzheimer's disease, and diabetes. However, the underlying mechanisms of the diet is still largely unknown.

The role of medium chain fats, provided in the diet, involving direct inhibition of a key neurotransmitter receptor (the AMPA receptor), and through regulating cellular energy through PPARγ activation and mitochondrial biosynthesis have provided alternative therapeutic approach that need to be explored. Understanding the role of AMPA, PPAR and mitochondrial biosynthesis, in relation to MCT ketogenic diet-responsive disorders may provide novel therapeutic targets and facilitate the development of new pharmacological and dietary treatments to achieve long-term remission from epileptic seizures.

Recently, it has been accomplished that decanoic acid has antiseizure effects at clinically relevant concentrations in vitro and in vivo [*Neuropharmacology*. 2013 June; 69:105-14]. Further in vivo pharmacokinetic data indicates that decanoic acid penetrates the blood-brain barrier. The data suggests that decanoic acid directly contributes to the therapeutic effect of the MCT ketogenic diet. Indeed, decanoic acid is more potent than valproic acid (a branched chain fatty acid isomer of octanoic acid), that is commonly used in the treatment of epilepsy.

Decanoic acid has completely blocked epileptiform activity generated by decreasing GABAergic inhibition or potentiating NMDA receptor currents. This supports an antiseizure effect of the decanoic acid component of the MCT diet, rather than diet-derived ketones [*Dis Model Mech.* 2012 January; 5(1):115-24].

Further, decanoic acid acts as a non-competitive antagonist at therapeutically relevant concentrations, in a voltage- and subunit-dependent manner, to exhibit antiseizure effects. This inhibitory effect is likely to be caused by binding to sites on the M3 helix of the AMPA-GluA2 transmembrane domain; independent from the binding site of perampanel [*Brain*. 2016 February; 139(2): 431-443]. Decanoic acid, a component of medium chain triclycerides, contributes to seizure control through direct AMPA receptor inhibition.

Acute anticonvulsant or antiepileptic or antiseizure effects of decanoic acid (DA) also known as "capric acid", C10 fatty acid is reported in the state of art.

EP Patent Application No. 3644985A1 discloses decanoic acid for use in treating epilepsy, wherein the decanoic acid is used in combination with an AMPA receptor inhibitor that binds to the same AMPA receptor site as perampanel.

WO2018/189113A1 discloses a composition comprising a decanoic acid to octanoic acid ratio of 70:30 to 90:10 wt/wt for use in treating epilepsy or controlling epileptic seizures.

Further, it is reported that oral administration of C10 could increase anti-seizure activity in patients with MCT KD [*Epileptic Disord* 2019; 21 (4): 366-9]. Sodium caprate, a medium chain fatty acid, increases the paracellular permeability through enlarging the tight junctions, thereby expanding paracellular routes for water-soluble, low lipophilic, and poorly absorbable drugs [*AAPS PharmSciTech*. 2010 March; 11(1): 372-382].

Unlike buccal and rectal delivery, oral formulations containing absorption promoters have the additional technical hurdle, whereby the promoter and payload must be co-released in high concentrations at the small intestinal epithelium to generate significant but rapidly reversible increases in permeability.

Conversely, decanoic acid and its metallic salt such as sodium caprate are having certain physiological limitations. C10 has the capacity to cause superficial damage to the intestinal epithelium in vivo. Further, C10 should be safe for use in high concentrations in oral dosage forms that may need to be given repeatedly even on a long-term basis. However, it might not be advisable to administer C10 formulations contemporaneously with other drugs that have the potential to elicit gastrointestinal side effects (e.g., NSAIDs, alcohol, etc.), nor to subjects with inflammatory bowel disease where basal intestinal permeability is already increased.

Further, it is observed that fatty acids like DA or its sodium salts are unsuitable for chronic administration due to its acidic nature, poor palatability, and gastrointestinal side effects. To avoid acid or sodium overload, especially for long-term treatment, there is a need to find out alternative smooth administration approach where DA can be easily carried out through GI tract.

The inventors of the present invention have come up with enriched source of DA, in other words the inventors have found that prodrugs or precursors or inactive form of DA called "tridecanoin" or "tricaprin" provides significant amount of DA after administration unlike free DA or salts thereof and without any acidic overload. Tridecanoin or tricaprin is nothing but triacylglycerol in which capric acid (n-decanoic acid) is linked to glycerol by a three-molecule ester bond. This kind of triglyceride of DA provides suitable formulations to avoid acid overload in patients.

Interestingly, the use of triglycerides of octanoate (trioctanoin) and decanoate (tridecanoin) in "a regular non-ketogenic diet" shows anticonvulsant effect. Particularly, tridecanoin is anticonvulsant, antioxidant, and improves mitochondrial function [*J Cereb Blood Flow Metab*. 2017 June; 37(6): 2035-2048].

Currently, it is believed that sustained neuronal electrical activity and seizures can lead to neuronal injury and death resulting from underlying biochemical mechanisms such as the formation of excessive ROS. This leads to oxidative stress-induced abnormal structural alterations of cellular proteins, membrane lipids, DNA, and RNA. Oxidative stress is an underlying mechanism in the initiation and progression of epilepsy and contributes to neuronal degeneration in the epileptic focus.

The generation of ROS following seizures and their contributions to seizure development and seizure-induced neuronal loss are measured by the free radical levels. The epileptiform activity results in free radical production and could be considered as a factor that induces cell death.

It is observed that NRF2-antioxidant response element (ARE) signalling pathway could represent an important target in protecting the brain from the damage induced by epileptic seizures. The NRF2 pathway has been considered for the treatment of epilepsy due to the presence of oxidative stress from altered steady-state glutathione levels during epileptogenesis. Moreover, the ketogenic diet profoundly alters redox processes, in part by increasing cellular glutathione levels via NRF2 pathway activation. Therefore, a clear rationale exists for validating the NRF2 pathway as antiepileptic or antiepileptogenic therapies.

Wang et al. [*Brain Res.* 2014; 1544:54-61] evaluates the NRF2-ARE signalling pathway activation for protecting brain from seizure-mediated damage and ameliorating cognitive impairment and oxidative stresses induced by epileptic seizures by employing NRF2 activator-sulforaphane (SF).

Various antioxidant agents could provide neuroprotective effects in a variety of neurological diseases through the activation of the NRF2-ARE pathway. EP Patent Application No. 3573968A1, provides tetrahydroisoquinoline derivatives as NRF2 activators. U.S. Pat. No. 9,737,525B2 discloses sulfanyl tiazole molecules as activators of the NRF2/KEAP1/ARE for treating a neurodegenerative disorder.

A hybrid of melatonin and sulforaphane combines the effects of melatonin with NRF2 induction properties, for achieving improved neuroprotective properties [*Journal List Br J Pharmacol.* 2015 April; 172(7): 1807-1821]. Activation of NRF2 with sulforaphane has recently gained attention as a new therapeutic approach in the treatment of many diseases, including epilepsy. As a plant-derived compound, sulforaphane is considered to be safe and well-tolerated. [*Toxicol Appl Pharmacol.* 2017 Jul. 1; 326:43-53].

In view of the above, it is evident that mere use of one therapeutic target could not be sufficient to give significant result in neurological diseases like epilepsy, wherein AMPAR antagonist is not enough to protect from oxidative stress damage, reversely NRF2 activators have limitations in order to regulate neuronal hyperexcitability and synchrony in seizure conditions.

Astonishingly, the inventors of the present invention have developed innovative therapeutic approach by introducing exogenous blend comprising specific combination of AMPAR antagonist and NRF2 activators that ameliorate natural defense mechanisms in synergistic manner for managing progression of epileptogenesis without any side effects.

OBJECTIVES OF THE PRESENT INVENTION

The primary objective of the present invention is to provide a promising therapeutic approach, for treating seizure related disorders.

Another objective of the invention is to provide a cost-effective, side-effect-free nutritional composition for treating neurological condition characterized by two or more unprovoked seizures or recurrent seizures.

Yet another object of the invention is to provide a nutrient based approach enriched with triglyceride and antioxidant for reducing the progression of epileptogenesis or fibrosis.

Further objective of the invention is to provide a combination of biologically active, safe, non-toxic, and naturally derived nutrients for treating epileptic seizures.

Another objective of the invention is to provide natural treatment in patients with epileptic seizures that leads to seizure-free status without adverse effects.

Yet another object of the invention is to provide natural remedy for treating chronic inflammatory diseases like fibrosis.

SUMMARY OF THE PRESENT INVENTION

To meet the above objectives, the inventors of the present invention carried out thorough experiments to establish significant effects of the bioactive ingredients or food ingredients or nutrients or exogenous naturally safe agents present in the composition that ameliorate abnormally excessive or synchronous neuronal activity in the brain.

In a particular aspect, the invention relates to synergistic nutritional compositions comprising therapeutically active nutrients along with pharmaceutically acceptable carriers for regulating unusual electrical activity in the brain.

In another particular aspect, the invention provides novel synergistic nutritional compositions comprising synergistic combination of non-competitive α-amino-3-hydroxy-5-methyl-4-isoxazolepropionic acid (AMPA) receptor antagonists; and nuclear factor erythroid 2-related factor 2 (NRF2) activators, present in suitable weight ratio, along with pharmaceutically acceptable excipients, wherein AMPAR antagonists are precursors of decanoic acid or triglycerides of decanoic acid such as tridecanoin or tricaprin; and (NRF2) activators are selected from the group consisting of L-ergothioneine, isothiocyanate, melatonin either alone or combination thereof.

In another aspect, the present invention provides naturally occurring saturated fatty acid based synergistic nutritional compositions for regulating sudden, uncontrolled electrical disturbance in the brain (epileptic seizures).

In exemplary aspect, the present invention provides nutritional antiepileptic/antiseizure remedy comprising synergistic combination of tricaprin and ergothioneine, which are present in specific weight ratio, along with pharmaceutically acceptable carriers.

In the present invention, the AMPA receptor antagonist markedly reduces or abolishes epileptiform by reducing neuronal hyperexcitability and regularizing voltage-gated ion channels (VGICs). Further, AMPA receptor antagonist increases ATP turnover and proton leak in mitochondria, which reduces oxidative stress to protect the brain from seizures and damage.

Simultaneously, NRF2 activator inhibits seizure-induced neuronal cell death by regulating NRF2/KEAP1/ARE antioxidant signalling pathway that protects neurons against oxidative damage and excitotoxic damage. The NRF2-ARE signalling pathway activation blocks reactive oxygen species or ROS production, mitochondrial depolarization, and cell death in a subject with a sudden surge of electrical activity in the brain.

In another aspect, the invention provides a cost effective, non-toxic, efficient and environmentally safe, exogenous nutritional composition comprising synergistic combination of food grade ingredients for reducing neuronal hyperexcitation and neuronal loss associated with seizures without adverse effects that are generally related to first- and second-generation AEDs.

In further aspect, the present invention provides novel and potent synergistic nutritional composition for treating fibrotic conditions.

In yet another aspect, the invention relates to synergistic nutritional compositions comprising combination of AMPAR antagonist which is present in a range of 1 to 5000 mg; and NRF2 activator which is present in a range of 1 to 1000 mg along with pharmaceutically acceptable excipients/carriers, optionally in presence of bioenhancer.

In yet one more aspect, the invention provides synergistic medicinal composition which is useful for treating seizure disorders such as epilepsy, reflex epilepsy, epileptic seizures, nonepileptic seizures, provoked seizures, idiopathic generalized epilepsy, convulsion, absence seizures, atonic seizures, tonic seizures, clonic seizures, myoclonic seizures, febrile seizure, focal seizures, temporal lobe seizures, occipital lobe seizures, parietal lobe seizures, nocturnal epilepsy, fibrotic diseases and mitochondrial dysfunction in diabetes.

ABBREVIATIONS

DA: Decanoic acid/Capric acid/C10
MCT: Medium-chain triglyceride
NRF2: Nuclear factor erythroid 2-related factor 2
NFE2L2: Nuclear factor erythroid-derived 2-like 2
KEAP1: Kelch-like ECH-associated protein 1
ARE: Antioxidant response element
AMPA: α-amino-3-hydroxy-5-methyl-4-isoxazolepropionic acid
AMPAR: α-amino-3-hydroxy-5-methyl-4-isoxazolepropionic acid receptors
NMDA: N-methyl-D-aspartic acid
GABA: Gamma-aminobutyric acid
PPAR-γ/PPARG: Peroxisome proliferator-activated receptor gamma
EGT: L-ergothioneine
SFN: Sulforaphane
KD: Ketonic Diet
GPR84: G-protein coupled receptor 84/proinflammatory receptor
GPR40: G-protein coupled receptor 40/Free fatty acid receptor 1 (FFA1)

BRIEF DESCRIPTION OF THE DRAWINGS

FIG. 1 illustrates a schematic representation of synergistic effect of AMPAR antagonist and NRF2 activator in epilepsy suppression.

FIG. 2 illustrates tonic convulsion time (seconds) with test treatment G1-normal control, G2-disease control, G3-reference (Levetiracetam), G4-Test I (Tridecanoin), G5-Test II (L-Ergothioneine), G6-combination (Tridecanoin+L-Ergothioneine)

FIG. 3 illustrates tonic convulsion time (seconds) with test treatment G1-normal control, G2-disease control, G3-reference (Levetiracetam), G4-Test I (Tridecanoin), G5-Test II (L-Ergothioneine), G6-combination (Tridecanoin+L-Ergothioneine)

FIG. 4 illustrates stupor phase time (seconds) with test treatment G1-normal control, G2-disease control, G3-reference (Levetiracetam), G4-Test I (Tridecanoin), G5-Test II (L-Ergothioneine), G6-combination (Tridecanoin+L-Ergothioneine)

DETAILED DESCRIPTION OF THE INVENTION

The invention will now be described in detail in connection with certain preferred and optional embodiments, so that various aspects thereof may be more fully interpreted and comprehended.

However, any skilled person or artisan will appreciate the extent to which such embodiments could be generalized in practice. It is further to be understood that all terminology used herein is for the purpose of describing particular embodiments only and is not intended to be limiting in any manner or scope.

Unless defined otherwise, all technical and scientific expressions used herein have the same meaning as commonly understood by one of ordinary skill in the art to which embodiments of the invention pertain. In describing and claiming the embodiments of the present invention, the following terminology will be used in accordance with the definitions set out below which are known in the state of art.

The singular forms "a," "an," and "the" include plural reference unless the context clearly dictates otherwise. Also, the term "composition" does not limit the scope of the invention for multiple compositions that can be illustrated for best mode of the invention.

The term "pharmaceutically/nutraceutically acceptable salt" as use herein, represents those salts which are within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, alkali or alkaline earth metal salts, as well as solvates, co-crystals, polymorphs and the like of the salts.

All modifications and substitutions that come within the meaning of the description and the range of their legal equivalents are to be embraced within their scope. A description using the transition "comprising" allows the inclusion of other elements to be within the scope of the invention.

The term "non-competitive antagonists" relates to a type of insurmountable antagonist that may act in one of two ways: by binding to an allosteric site of the receptor or by irreversibly binding to the active site of the receptor. Further when antagonists act at an allosteric site, these bind to a distinctly separate binding site from the agonist, exerting their action to that receptor via the other binding site. They do not compete with agonists for binding at the active site. The bound antagonists may prevent conformational changes in the receptor required for receptor activation after the agonist binds.

In a preferred embodiment, the present invention provides novel, potent synergistic nutritional composition for treating seizure disorders, comprising combination of non-competitive AMPAR antagonists and NRF2 activators present in suitable weight ratio, along with pharmaceutically acceptable excipients.

Particularly, the synergistic effect is achieved by targeting two pathways, which include blocking voltage dependent AMPA receptor channels; simultaneously activating NRF2-ARE signaling pathway to prevent or reduce the progression of epileptogenesis.

In another preferred embodiment, the invention provides synergistic nutritional composition comprising exogenous blend of AMPAR antagonists and NRF2 activators present in suitable weight ratio, along with pharmaceutically acceptable excipients.

The term "AMPA receptor antagonist" refers to the α-amino-3-hydroxy-5-methyl-4-isoxazolepropionic acid receptor (also known AMPAR), is an ionotropic transmembrane receptor for glutamate that mediates fast synaptic transmission in the central nervous system (CNS). It is a non-NMDA-type receptor. AMPAR antagonists are anticonvulsants used in patients with epilepsy in the treatment of partial-onset seizures.

They are non-competitive antagonists of AMPA receptors, a type of glutamate receptor that participates in excitatory neurotransmission. In the present invention precursors of DA i.e., tridecanoin is used as AMPAR antagonist.

The term "non-competitive antagonist" relates to ionotropic glutamate receptors, an inhibitor whose blocking action is not reduced progressively as the agonist (glutamate) concentration is increased as occurs for competitive antagonists. Non-competitive antagonists allosterically inhibit the channel by binding to a site other than the ligand binding domain.

The term "NRF2" connotes Nuclear factor erythroid 2-related factor 2 (NRF2), also known as nuclear factor erythroid-derived 2-like 2, is a transcription factor that in humans is encoded by the NFE2L2 gene. NRF2 regulates the expression of antioxidant proteins that protect against oxidative damage triggered by injury and inflammation. NRF2 activator stimulate the NFE2L2 pathway and useful for treatment of diseases that are caused by oxidative stress.

In one preferred embodiment, the invention provides synergistic nutritional composition, wherein non-competitive AMPAR antagonists are precursors of decanoic acid or triglycerides of decanoic acid called tridecanoin or tricaprin.

Tricaprin is an orally available precursor of decanoic acid (DA), a 10-carbon fatty acid and major component of medium chain triglyceride oils.

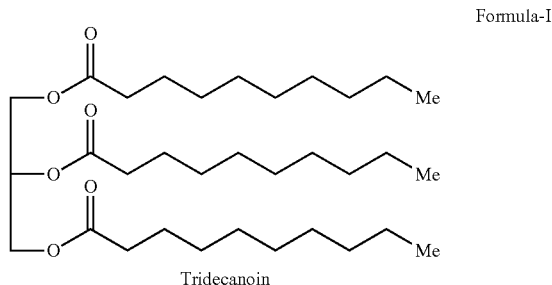 [SMILES: CCCCCCCCCC(=O)OCC(COC(=O)CCCCCCCCC)OC(=O)CCCCCCCCC]

Formula-I

Tridecanoin

Triglycerides of decanoic acid called tridecanoin or tricaprin has a molecular formula $C_{33}H_{62}O_6$ and is represented above as Formula-I. Decanoic acid (capric acid) is a medium-chain fatty acid found in saturated fats (cow butter, and plant oils like coconut oil). Capric acid is a major constituent of the MCT ketogenic diet, providing about 40% of the medium chain fat within the diet. This acid shows positive effect on seizure control through direct AMPA receptor inhibition and on mitochondrial diseases through the binding to PPARgamma. It readily crosses the blood-brain barrier, probably by a combination of diffusion and saturable carrier-mediated transport via a medium-chain fatty acid transporter.

In the present invention, tridecanoin acts as a non-competitive AMPA receptor antagonist present in therapeutically effective amount. "Tridecanoin" or "Tricaprin" is an orally available precursor of decanoic acid (DA). Upon oral administration, tricaprin is hydrolyzed to DA, which allosterically binds to transmembrane domain site. Notably, oral ingestion of tricaprin is associated with a significant release of DA in the circulation, both in esterified and non-esterified forms. The result implies that the prolonged use of tricaprin promotes the transportation of DA primarily in the esterified form. The triglyceride of DA reduces action potential (AP) firing of hippocampal pyramidal neurons by inhibiting voltage-gated ion channels. The term "tridecanoin induced DA" or "tridecanion triggered DA" or "precursor of DA" relates to DA which is released with excellent transit rate in the GI tract after oral administration of effective amount of tridecanion without any acid overload.

The DA release from triglyceride reduces neuronal excitability by inhibition of AMPA receptor activity; importantly, it is shown that tridecanoin, act as a non-competitive AMPA receptor antagonist, where the hydrolyzed DA binds to a site that is distinct from the perampanel binding site of the receptor. These findings confirm the existence of a powerful anticonvulsant mechanism of medium chain triglyceride ketogenic diets, which is based on the direct inhibition of excitatory neurotransmission by tridecanoin.

It is further evident that PPARγ is activated by fatty acids, such as decanoic acid, and might therefore mediate anti-inflammatory and antioxidant properties of the ketogenic diet (KD) (i.e., high-fat, low-carbohydrate, and adequate-protein diet). Tridecanoin triggered DA acts as PPARγ agonist that confers seizure protection. Since seizure suppression is associated with a PPARγ induced increase in PPARγ2 expression, eventually contributes to the anti-seizure effects of KD therapy.

Further, the supplementation of fibroblast cells with decanoic acid precursors has pleiotropic effects on mitochondrial function through targeting the PPAR-γ receptor, and thus potentially increasing mitochondrial biogenesis as well as increasing cellular resistance to oxidative stress. The tridecanoin induced DA also activates PPAR-alpha and PPAR-beta/delta, that may improve insulin sensitivity.

In light of the above, a role for decanoic acid as a PPARγ agonist may also provide a therapeutic effect in treatment of diabetes. Thus, increasing mitochondrial content through tridecanoin induced DA treatment, in conjunction with improved mitochondrial function and increased antioxidant capacity that forms endogenous defence against the deleterious effects of mitochondrial dysfunction in diabetes.

In certain embodiments, the invention provides tridecanoin as AMPAR antagonists, wherein they markedly reduce or abolish epileptiform by reducing neuronal hyperexcitability and regularizing voltage-gated ion channels (VGICs). AMPA receptor inhibition by tridecanoin induced DA is voltage-dependent and is more effective at depolarized potentials. This voltage dependence confirms that the therapeutic effect of tridecanoin in reducing AMPA receptor currents is enhanced during post-synaptic activation and seizure propagation. This result also establishes that the binding site for decanoic acid lies in or near to the channel region of the receptor and is consistent with the properties of known AMPA receptor pore blockers such as the polyamines.

It is further indicated that tridecanoin induced DA binds by means of hydrogen bonding between its two carboxylic acid oxygens and the two hydrogens of the cyclic amine group of proline at residue position on each of the four M3 helices subunits within the ion channel. It is likely that the binding of decanoic acid to each of the four subunits cooperatively contributes to its therapeutic effects.

Additionally, the inventors have found that the triglyceride of decanoic acid enhances the rate of mitochondrial respiration and ATP turnover, results improvement in mitochondrial function. An increase in mitochondrial activity can lead to exacerbated generation of free radicals, resulting in oxidative stress. Therefore, if ATP generation is enhanced it is important to keep free radicals at bay to prevent oxidative stress, which can be achieved by increasing proton leakage over the mitochondrial membrane. Remarkably tridecanion triggered DA increases ATP turnover and proton leak in mitochondria which leads to increase in UCP protein levels or activation of UCPs. Moreover, up regulation of uncoupling protein 2 (UCP2) prevents neuronal death including that occurring during seizures.

Notably the potency of decanoic acid dependent AMPA receptor inhibition is independent of increased glutamate during seizure activity. In yet another embodiment, the invention provides synergistic nutritional composition comprising therapeutically effective amount of tridecanoin. The dose to be administered usually ranges from 1 mg to 5000 mg, preferably 10 mg to 3000 mg, more preferably 100 mg to 2500 mg per day. The total dose of the medicament containing tridecanoin for adult is 5-50 mg/kg every day.

In another preferred embodiment, the invention provides potent synergistic nutritional composition, wherein NRF2 activators are selected from the group consisting of L-ergothioneine (represented below as Formula-II), isothiocyanate (represented below as Formula-III), DL sulforaphane (represented below as Formula-IV) and melatonin (represented below as Formula-V) which are present either alone or salts thereof or combinations thereof.

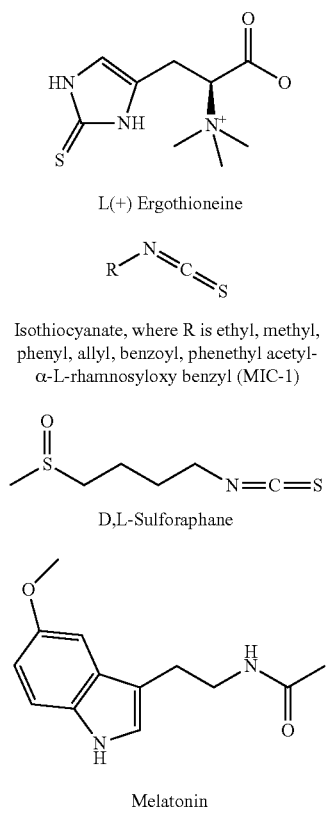

Formula-II

L(+) Ergothioneine

Formula-III

Isothiocyanate, where R is ethyl, methyl, phenyl, allyl, benzoyl, phenethyl acetyl-α-L-rhamnosyloxy benzyl (MIC-1)

Formula-IV

D,L-Sulforaphane

Formula-V

Melatonin

In the present invention the NRF2 activators are obtained or derived from natural sources that avoid drug toxicity. Particularly "L-ergothioneine" is a naturally occurring amino acid and is a thiourea derivative of histidine, containing a sulfur atom on the imidazole ring. Ergothioneine is found in food like include black beans, kidney bean, and oat bran, with the highest levels in bolete and oyster mushrooms. Isothiocyanates are amino acid derivatives that contain the monovalent group-NCS. Isothiocyanates are derived from the hydrolysis of glucosinolates-(sulfur-containing compounds) found in cruciferous vegetables. Isothiocyanates are selected from the group consisting of ethyl, methyl, phenyl, allyl, benzoyl, phenethyl, acetyl-α-L-rhamnosyloxy rhamnosyloxy benzyl (MIC-1) substituted isothiocyanates.

Many isothiocyanates, particularly sulforaphane, have been shown to induce the expression of antioxidant enzymes via the activation of the Nuclear factor erythroid 2-related factor 2 (NRF2)-dependent pathway. Particularly, NRF2 is a transcription factor that is bound to the protein Kelch-like ECH-associated protein 1 (KEAP1) in the cytosol. KEAP1 responds to oxidative stress signals or chemical inducers by freeing NRF2. Isothiocyanates can react with sulfhydryl residues of KEAP1, causing the release of NRF2. "Sulforaphane" i.e., 1-Isothiocyanato-4-(methanesulfinyl) butane is a natural plant compound found in many cruciferous vegetables like broccoli, cabbage, cauliflower, and kale.

Additionally, "Melatonin" has been identified in many plants including feverfew (*Tanacetum parthenium*), and St John's wort (*Hypericum perforatum*) as well as in some fruits and grains like bananas and grapes, rice, wheat, barley, and oats are rich in melatonin. Other foods include herbs, olive oil, coffee, tea, wine, and beer.

According to the invention, NRF2 activators reduce seizure-induced neuronal cell death by regulating NRF2/KEAP1/ARE antioxidant signaling pathway that protects neurons against oxidative damage and excitotoxic damage. The NRF2-ARE signaling pathway activation inhibits reactive oxygen species ROS production, mitochondrial depolarization, and cell death in a subject with seizure-like symptoms.

Antioxidants have been suggested as therapeutic strategies for the treatment and modulation of epilepsy. In the present invention, NRF2 acts as a primary cellular defender against the cytotoxic effects of oxidative stress. Moreover, it acts as potent antioxidant that represses the formation of excessive ROS and protect the cells from oxidative damage.

Notably under conditions of homeostasis, NRF2 is retained in the cytosol, bound to a cluster of proteins that includes its cytosolic inhibitor KEAP1, when stimulated it dissociates from KEAP1 and moves to the nucleus to bind with ARE to regulate the transcription of antioxidant genes.

It is further observed that under non-stressed conditions, the NRF2 transcription factor is covalently bound to cysteine residues on its native repressor KEAP1 in the cytoplasm. This results in the degradation of NRF2 and inhibition of the antioxidant response. But under oxidative stress conditions cysteine residues on KEAP1 are modified, resulting in the stabilization and translocation of NRF2 into the nucleus, where it can bind to the promoter region of the ARE and initiate the transcription of various cytoprotective enzymes which function to promote cellular survival through a mechanism called NRF2/KEAP1/ARE, favoring dissociation of NRF2 and subsequent nuclear translocation, including the upregulation of antioxidant function, inflammatory inhibition, and the transport of toxic metabolites. Activation of NRF2 has been shown to regulate important cellular antioxidant genes and protect the cells from oxidative damage.

In yet another embodiment, the invention provides synergistic nutritional composition comprising therapeutically effective amount of naturally derived NRF2 activators. The dose to be administered usually ranges from 1 mg to 1000 mg, preferably 10 mg to 500 mg per day.

As used herein, the term "therapeutically effective amount" is intended to mean that, "the amount of active biological compounds or nutrients used in the present invention are significantly more effective for regulating abnormal electrical discharge/signals/impulses of brain cells, when used in the combination with suitable weight ratio".

The present nutritional composition synergistically controls or regulate abnormal electrical signals that interrupts normal electrical brain function. It supports to balance brain's electrical rhythms.

In another embodiment the invention provides synergistic nutritional composition, wherein the composition is useful for treating seizure disorders such as epilepsy, reflex epilepsy, epileptic seizures, nonepileptic seizures, provoked seizures, idiopathic generalized epilepsy, convulsion, absence seizures, atonic seizures, tonic seizures, clonic seizures, myoclonic seizures, febrile seizure, Generalized seizures, focal seizures, Absence seizures (also called petit mal seizures), temporal lobe seizures, atonic seizures (drop attacks), generalized tonic-clonic seizure (GTC or also called grand mal seizures), Febrile seizures occipital lobe seizures, parietal lobe seizures, Frontal lobe epilepsy, Temporal lobe epilepsy, nocturnal epilepsy, Neocortical epilepsy, infantile spasms Hypothalamic hamartoma, fibrotic diseases and insulin regulation.

The term fibrosis describes the development of fibrous connective tissue as a reparative response to injury or damage. It is the overgrowth, hardening, and/or scarring of various tissues and is attributed to excess deposition of extracellular matrix components including collagen. Fibrosis may refer to the connective tissue deposition that occurs as part of normal healing or to the excess tissue deposition that occurs as a pathological process. When fibrosis occurs in response to injury, the term "scarring" is used i.e., thickening of the tissue. Repeated injuries, chronic inflammation and repair are susceptible to fibrosis where an accidental excessive accumulation of extracellular matrix components, such as the collagen is produced by fibroblasts, leading to the formation of a permanent fibrotic scar. Fibrosis is the result of chronic inflammatory reactions induced by a variety of stimuli including persistent infections, autoimmune reactions, allergic responses, chemical insults, radiation, and tissue injury.

Fibrogenesis can result from an increase in the growth of fibroblasts, an increase in the rate of collagen synthesis, or a decrease in the rate of collagen degradation. In some embodiment, the invention provides synergistic nutritional composition, wherein tridecanoin induced decanoic acid target on key signaling pathways that regulate fibrogenesis. Particularly it regulates GPR40 and GPR84 major mediators in pathologic fibrotic pathways. GPR40 and GPR84 are G protein-coupled receptors with free fatty acid ligands and are associated with metabolic and inflammatory disorders.

The synergistic nutritional composition significantly attenuate fibrosis observed in kidney, liver, lung, heart, pancreas, brain, heart, muscle, colon, thymus, spleen, intestine, placenta and skin. It is likely that GPR40 and GPR84 modulate profibrotic, inflammatory and epithelial-mesenchymal transition processes. Therefore, GPR40 may partially protect against development of fibrosis, whereas GPR84 may induce the promotion and stimulation of fibrosis.

The present synergistic nutritional composition acts as an agonist for GPR40 and as an antagonist or inverse agonist for GPR84, and it inhibits fibrosis in several models of tissue fibrosis. Further it is useful in the signs of kidney injury in an accelerated model of diabetic nephropathy.

In some embodiment, the invention provides synergistic nutritional composition comprising an effective amount of triglycerides of decanoic acid i.e. tricaprin or tridecanoin in a pharmaceutically acceptable carrier is administered to a mammal, particularly a human, to significantly increase the protection of the kidneys or sole healthy kidney. Particularly it reduces progression of chronic kidney diseases which includes the treatment of kidney diseases associated with nephrectomy, renal fibrosis, glomerular sclerosis, and end stage renal disease. Further includes the treatment of renal failure progression associated with hypertension, infarct, tumor, diabetes mellitus, autoimmunity, or inflammation.

The capric triglyceride can also be used for preparing the medicament for treating alcoholic fatty liver disease (ALFD).

In certain embodiment, the invention provides synergistic nutritional composition comprising effective amount NRF2 activators that further regulate the expression of genes promoting mitochondrial biogenesis such as mitochondrial transcription factors and are therefore directly involved in mitochondrial preservation. The naturally derived compounds such as L-ergothioneine, isothiocyanate, sulforaphane, melatonin are effectively restoring the impaired or disrupted NRF2 signalling pathway.

In one preferred embodiment, the invention furnishes potent and stable synergistic nutritional compositions, wherein the composition comprising therapeutic combinations of effective amount of non-competitive AMPA receptor antagonists and NRF2 activators, which are present in the weight ratio of 1:0.001 to 1:0.5 along with pharmaceutically acceptable excipients.

In one preferred embodiment, the invention provides synergistic novel nutritional composition comprising non-competitive AMPA receptor antagonists and NRF2 activators, wherein non-competitive AMPA receptor antagonist is triglyceride and NRF2 activators are selected from group L-ergothioneine, isothiocyanate, sulforaphane, melatonin either alone or in combination.

In another preferable embodiment, the invention provides novel and potent synergistic nutritional composition wherein the triglyceride is tridecanoin and NRF2 activator is white crystalline L-ergothioneine present in the weight ratio of 1:0.001 to 1:0.5 along with pharmaceutically acceptable excipients.

In another embodiment, the invention furnishes the potent synergistic nutritional composition, wherein the composition comprising therapeutic exogenous combinations of effective amount of tridecanoin and L-ergothioneine, which are present in the weight ratio of 1:0.001 to 1:0.5 along with pharmaceutically acceptable excipients.

In additional embodiment the composition further comprises sulforaphane or melatonin or combination thereof.

In another preferred embodiment, the invention provides synergistic nutritional compositions for treating conditions associated with seizure and fibrosis comprising therapeutically effective combination of tridecanoin and L-ergothioneine present in the weight ratio of 1:0.001 to 1:0.5 along with pharmaceutically acceptable excipients.

In one more embodiment, the invention provides a synergistic nutritional composition comprising effective amount of tridecanoin present in a range of 50% to 99% by weight of the total composition.

In one more embodiment, the invention provides a synergistic nutritional composition comprising effective amount of NRF2 activators selected from groups L-ergothioneine, sulforaphane, melatonin either alone or in combinations present in a range of 0.5% to 10% by weight of the total composition.

In another preferred embodiment, the invention provides stable, orally active anticonvulsant or anti-seizure or anti-epileptic nutritional compositions comprising synergistic combination of therapeutically effective amount of tridecanoin and L-ergothioneine, wherein the tridecanoin and the L-ergothioneine are present in the weight ratio of 1:0.002 to 1:0.2 along with pharmaceutically acceptable excipients. In a preferred embodiment, the excipients are selected from a group consisting of a diluent present in a range of 1 to 25%; a binder present in a range of 0.1 to 20%; a lubricant present in a range of 0.1 to 5.0%; a glidant present in a range of 0.1 to 5.0%; an additive present in a range of 1 to 5%; a surfactant present in a range of 0.1 to 5.0%; a stabilizer present in a range of 0.1 to 5.0%; a plasticizer present in a range of 0.1 to 5.0% by weight of total composition.

In yet another preferred embodiment, the invention provides stable, orally active antifibrotic nutritional compositions comprising synergistic combination of therapeutically effective amount of tridecanoin and L-ergothioneine, wherein the tridecanoin and the L-ergothioneine are present in the weight ratio of 1:0.002 to 1:0.2 along with pharmaceutically acceptable excipients. In a preferred embodiment, the excipients are selected from a group consisting of a diluent present in a range of 1 to 25%; a binder present in a range of 0.1 to 20%; a lubricant present in a range of 0.1 to 5.0%; a glidant present in a range of 0.1 to 5.0%; an additive present in a range of 1 to 5%; a surfactant present in a range of 0.1 to 5.0%; a stabilizer present in a range of 0.1 to 5.0%; a plasticizer present in a range of 0.1 to 5.0% by weight of total composition.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum CRP level), and/or minimize at least one clinical symptom related to seizure conditions.

The term "subject in need thereof" pertains to subject preferably mammal, more preferably human suffering or suspected with neurological disorders, particularly with seizures, where the normal electrical pattern is disrupted by sudden and synchronized bursts of electrical energy.

Particularly, the subject is human with pre-existing or onset symptoms of seizures or in a subject to prevent occurrence of seizures or subject with AED intolerance or AED medication side effects.

In the context of the present invention, the term "treatment" relates to alleviate, mitigate, prophylaxis, attenuate, manage, regulate, modulate, control, minimize, lessen, decrease, down regulate, up regulate, moderate, inhibit, restore, suppress, limit, block, decrease, prevent, inhibit, stabilize, ameliorate, or cure, heal the abnormal neuronal firing and neuronal damage observed in patients with seizures.

Notably, the present synergistic composition is non-hazardous, non-toxic, food ingredient and safe for human consumption without any adverse effects, therefore the present nutritional composition can also be used under preventive therapy/adjuvant therapy/add-on therapy/combination/adjunctive therapy in a subject in need thereof.

Certain compounds of the present invention can exist in unsolvated forms as well as solvated forms, including hydrated forms. Further some compounds of the present invention can exist in multiple crystalline or amorphous forms ("polymorphs"). In general, all physical forms are of use in the methods contemplated by the present invention and are intended to be within the scope of the invention. Compound or a pharmaceutically acceptable salts, hydrates, polymorphs or solvates of a compound intends the inclusive meaning of "or", in that materials meeting more than one of the stated criteria are included, e.g., a material that is both a salt and a solvate is encompassed.

Compounds of the invention can exist in particular geometric or enantiomeric or stereoisomeric forms. The invention contemplates all such compounds, including dextrorotatory and levorotatory-isomers, rectus, and sinister configuration. All such isomers, as well as racemic mixtures thereof, are intended to be included in this invention.

As used herein, the term "pharmaceutically acceptable carriers, diluents or excipients" is purported to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic nutritional composition, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal, or oral.

In some embodiment, the present synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. Further the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a a bolus, electuary or paste, nutritional bar, energy bars (candy bars), powder, granule sachet.

Further the present composition can be formulated in the form of age-appropriate pediatric oral dosage forms such as syrup, minitablets, chewable formulations, orodispersible films orodispersible tablets. It can also be prepared in the form of snack, chocolate bars or other confectionery food products.

In the context of the present invention, the terms "treatment" and the like refer to alleviating, mitigating, prophylaxis, attenuating, managing, regulating, modulating, controlling, minimizing, lessening, decreasing, down regulating, up regulating, moderating, inhibiting, suppressing, reversing, reducing, limiting, blocking, preventing, inhibiting, stabilizing, ameliorating, or curing, healing the convulsion disorders.

Notably, the present synergistic composition is stable, non-hazardous, non-toxic and safe for human consumption without any side effects, therefore the present nutritional composition can also be used under preventive therapy/adjuvant therapy/add-on therapy/combination therapy in a subject in need thereof.

In another embodiment, the synergistic composition of the present invention is non-toxic, cost effective, enriched with nutrients or biomolecules, and provides safeguard against uncontrolled electrical disturbance in the brain, without any adverse effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose(HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1 to 40% by weight of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 5.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In another embodiment of the invention, the amount of solubilizing agent or surfactant in the composition/formulation ranges from 0.1% to 10% by weight of the composition/formulation. In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 8.0% by weight of the total composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, acetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used. In a preferred embodiment of the invention, the additives are used in a range of 1 to 20% w/w of unit dose.

In yet another embodiment, the invention provides a synergistic nutritional composition comprising a therapeutic blend of a biotin-manganese complex and a stabilized oxaloacetate along with pharmaceutical excipients, wherein the pharmaceutical excipients are selected from a diluent, a binder, a lubricant, a glidant, an additive, a surfactant, a stabilizer, or mixtures thereof.

In a preferred embodiment, a diluent is present in a range of 1 to 30%; a binder present is present in a range of 0.1 to 25%; a lubricant is present in a range of 0.1 to 5.0%; a glidant is present in a range of 0.1 to 5.0%; an additive is present in a range of 1 to 10%; a surfactant is present in a range of 0.1 to 5.0%; a stabilizer is present in a range of 0.1 to 5.0%; a plasticizer is present in a range of 0.1 to 5.0%, by weight of the total composition.

In a preferred embodiment, the present medicinal composition/formulation is formulated for oral administration. Specifically, the solid medicinal compositions are in the form of tablets, capsules, pills, hard capsules filled with liquids or solids, soft capsules, sachets, powders, granules, suspensions, solutions, or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

In a further embodiment, the present composition is formulated in the form of age-appropriate pediatric oral dosage forms such as syrup, bar, dietary supplements, fortify supplement drink, minitablets, chewable formulations, orodispersible films and orodispersible tablets.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 2500 mg per day, preferably about 10 mg per day to about 1000 mg per day. In some embodiments, the total daily dose can range from about 1 mg to about 5000 mg per day, and preferably about 2.5 mg to about 1000 mg per day.

In certain embodiments, the invention provides the potent synergistic medicinal composition wherein the effective unit dose for an oral administration is formulated in a range of 5 to 650 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust, or terminate therapy in conjunction with an individual patient's response.

The use of any and all examples, or exemplary language (e.g., "such as") provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway. The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Having described the basic aspects of the present invention, the following non-limiting examples illustrate specific embodiments thereof. Those skilled in the art will appreciate that many modifications may be made in the invention without changing the essence of invention.

Example-1 i. Composition 1: Synergistic blend

| Ingredient | w/w % |
| --- | --- |
| Tridecanoin | 50-99% |
| L-Ergothioneine | 0.1-10% | ii. Composition 2: Tablet/Capsule

| Ingredient | w/w % unit dose |
| --- | --- |
| Tridecanoin | 95% |
| L-Ergothioneine | 5% |
| Excipient | 5-10% |
| Average weight | 100% |
| Average weight in mg | 500-550 mg | iii. Composition 3: Tablet/Capsule

| Ingredient | w/w % unit dose |
| --- | --- |
| Tridecanoin | 90-98% |
| L-ergothioneine | 1-5% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | iv. Composition 4: Tablet/Capsule

| Ingredient | mg per unit dose |
| --- | --- |
| Tridecanoin | 500 |
| L-ergothioneine | 5 |
| Microcrystalline Cellulose | 1-20 |
| Silicon dioxide | 1-10 |
| Hydroxypropyl Methylcellulose | 1-10 |
| Zinc Stearate | 1-10 |
| PVP K-30 | 2-10 |
| 2-Hydroxypropy-β-cyclodextrin | 1-10 |
| Talc | 1-10 |
| Polysorbate 80 | 1-10 |
| Manitol | 1-20 |
| Propylene Glycol | QS |
| Water | QS |
| Average weight | 550-600 mg | v. Composition 5: Tablet/Capsule

| Ingredient | mg per unit dose |
| --- | --- |
| Tridecanoin | 250 |
| L-ergothioneine | 2.5 |
| Microcrystalline Cellulose | 1-20 |
| Silicon dioxide | 1-10 |
| Hydroxypropyl Methylcellulose | 1-10 |
| Zinc Stearate | 1-10 |
| PVP K-30 | 2-10 |
| 2-Hydroxypropyl-β-cyclodextrin | 1-10 |
| Talc | 1-10 |
| Polysorbate 80 | 1-10 |
| Manitol | 1-20 |
| Propylene Glycol | QS |
| Water | QS |
| Average weight | 300-400 | vi. Composition 6: Tablet/Capsule

| Ingredient | mg per unit dose |
| --- | --- |
| Tridecanoin | 500 |
| L-ergothioneine | 5 |
| Sulforaphane | 1 |
| Microcrystalline Cellulose | 1-20 |
| Silicon dioxide | 1-10 |
| Hydroxypropyl Methylcellulose | 1-10 |
| Zinc Stearate | 1-10 |
| PVP K-30 | 2-10 |
| 2-Hydroxypropyl-β-cyclodextrin | 1-10 |
| Talc | 1-10 |
| Polysorbate 80 | 1-10 |
| Manitol | 1-20 |
| Propylene Glycol | QS |
| Water | QS |
| Average weight | 550-600 | vii. Composition 7: Tablet/Capsule

| Ingredient | mg per unit dose |
| --- | --- |
| Tridecanoin | 250 |
| L-ergothioneine | 2.5 |
| Sulforaphane | 1.0 |
| Melatonin | 1.5 |
| Sodium ascorbate | 1-10 |
| Microcrystalline Cellulose | 2-20 |
| Betacyclodextrin | 1-5 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Manitol | 5-20 |
| Alcohol | QS |
| Water | QS |
| Average weight | 270-350 mg | viii. Composition 8: Tablet/Capsule

| Ingredient | mg per unit dose |
| --- | --- |
| Tridecanoin | 500 |
| L-ergothioneine | 2.5 |
| Melatonin | 2.5 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| Talc | 1-10 |
| Methyl-β-cyclodextrin | 1-10 |
| Polysorbate 80 | 1-10 |
| Manitol | 1-10 |
| IPA | QS |
| Water | QS |
| Average weight | 550-650 mg | ix. Composition 9: Tablet/Capsule/Syrup

| Ingredient | mg per unit dose |
| --- | --- |
| Tridecanoin | 100 |
| L-ergothioneine | 2.5 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| 2-Hydroxypropyl-β-cyclodextrin | 1-10 |
| Talc | 1-10 |
| Polysorbate 80 | 1-10 |
| Manitol | 1-10 |

-continued

| Ingredient | mg per unit dose |
|---|---|
| IPA | QS |
| Water | QS |
| Average weight | 125-150 mg |

Example 2: Animal Study

The purpose of this study is to evaluate the effect of anti-convulsant activity of the test compound in Wistar Rats.
Test System and Animal Husbandry
Species: Rats
Strain: Wistar
Sex: Male
No. of animals: 36 Animals (n=6 per group)
Body weight: 200-220 gm
CPC SEA Registration Number-1803/PO/RcBi/S/2015/CPC SEA
Animal House conditions
Lighting: 12/12-hour light-dark cycle
Temperature: 22±3° C.
Relative Humidity: 30 to 70%
Animals had continuous access to fresh, potable, uncontaminated drinking water.
Feed: Normal chow diet [PURINA 5L79 from PMI Nutritional, USA]
Group, Designation and Dose Levels
Phosphate-buffered saline [PBS] was used as a vehicle for test formulation.

TABLE 1

Animal grouping and treatment details

| Groups | Group Description | Dose Level [Rat] | No. of animals |
|---|---|---|---|
| Group 1 | Normal control | Phosphate-buffered saline | 6 |
| Group 2 | Diseased Control | Phosphate-buffered saline | 6 |
| Group 3 | Reference standard [Levetiracetam] | 50 mg/kg | 6 |
| Group 4 | Test I [Tridecanoin] | 51.66 mg/kg | 6 |
| Group 5 | Test II [L-Ergothioneine] | 0.52 mg/kg | 6 |
| Group 6 | Test I + Test II [Tridecanoin + L-Ergothioneine] | 51.66 mg/kg + 0.52 mg/kg | 6 |

Acclimatization

All rats were allowed to acclimatize to the experimental room conditions for at least five days prior to the commencement of dosing. During the acclimatization period animals were observed for any clinical signs prior to commencement of treatment. A detailed physical health examination was performed for all animals by a veterinarian and the animals with any evidence of ill health or poor physical condition were not chosen for the study.

Individual body weights were recorded at receipt, on the day of randomization, on the first day of treatment before dosing and weekly once thereafter throughout the treatment period. Terminal (fasting) body weights were taken on the day of scheduled necropsy. The body weight changes for all the animals were calculated and reported along with the body weight data.

Induction of PTZ (Pentylene-tetrazole)

The systemic administration of PTZ is one of the most commonly employed methods for anti-convulsant screening. The preference has been given to this model due to its ease of performance, reliability, ease of expressing results and the shorter time-period to produce convulsions.

60 mg/kg of PTZ was injected per body weight, intraperitoneally 1 hr after the test item administration.

The main mechanism involved in PTZ administration seems to relate to the inhibition of the inhibitory functions of the GABA neurotransmitter. PTZ has affinity towards the chloride ionophore of the post synaptic GABA receptor complex and to antagonize GABA nergic function.

Experimental Procedure:

All animals were acclimatized for five days and seizures were induced by administering 60 mg/kg PTZ per body weight, 1 hr after test item administration. Normal control group was injected with phosphate buffer solution.

As Group 1 (Vehicle control), Group 2 served as diseased control, Group 3 was Reference standard and Group 4, Group 5 and Group 6 served as test substance. The dose was administered for short term (single day administration) or long term (14 or 21 days) after acclimatization.

The time was recorded for convulsion phase clonic, tonic and stupor after test administration. All values were expressed as MEAN±STD. The significant difference between the treatment and control group was estimated using oneway ANOVA with Dennett's test. All results of the statistical analysis were summarized in separate tables.

Results:

TABLE 2

Overall effects of treatment determined by one-way ANOVA

| Grp. No. | Treatment Group | Tonic Convulsions (Seconds) | Straub Tail | Clonic Convulsions (Seconds) | Stupor (seconds) | Recovery |
|---|---|---|---|---|---|---|
| G1 | Normal control | 12.33 | Present | 7.33 | 121.00 | Recovery |
| G2 | Diseased Control | 21.33 | Present | 12.00 | 139.66 | Death |
| G3 | Reference standard (Levetiracetam 500 mg) | 5.83 | Absent | 3.33 | 56.16 | Recovery |
| G4 | Test I (Tridecanoin) | 7.66 | Absent | 5.00 | 74.16 | Recovery |
| G5 | Test II (L-Ergothioneine) | 8.00 | Absent | 4.66 | 70.33 | Recovery |

TABLE 2-continued

Overall effects of treatment determined by one-way ANOVA

| Grp. No. | Treatment Group | Tonic Convulsions (Seconds) | Straub Tail | Clonic Convulsions (Seconds) | Stupor (seconds) | Recovery |
|---|---|---|---|---|---|---|
| G6 | Test I + Test II (Tridecanoin + L-Ergothioneine) | 4.16 | Absent | 1.16 | 41.33 | Recovery |

DISCUSSION

It was clearly indicated that treatment with test substances (G4-G6) are able to lower the convulsion phases time. The reduction of tonic-clonic convulsion time observed in G6 is more significant than the reference G3 and individual components G4 and G5. The combination of G4 and G5 in specific ratio shows better anticonvulsant property at different phases in PTZ induced rat model. Thus, it is concluded that systemic administration of present composition produces synergistic anticonvulsant effects in seizure experimental models. Particularly the composition exhibits improved anticonvulsant effects with more than 70% efficacy.

We claim:

1. A novel, stable, synergistic nutritional composition comprising: a therapeutic exogenous combination of an effective amount of tridecanoin and white crystalline L-ergothioneine, present in a weight ratio of 1:0.001 to 1:0.5 along with pharmaceutically acceptable excipients.

2. The novel, stable, synergistic nutritional composition according to claim 1, wherein the tridecanoin is present in a range of 50% to 99% by weight of the total composition and the white crystalline L-ergothioneine is present in a range of 0.5% to 10% by weight of the total composition.

3. The novel, stable, synergistic nutritional composition according to claim 1, wherein the pharmaceutically acceptable excipients are selected from a group consisting of a diluent present in a range of 1 to 30%; a binder present in a range of 0.1 to 25%; a lubricant present in a range of 0.1 to 5.0%; a glidant present in a range of 0.1 to 5.0%; an additive present in a range of 1 to 10%; a surfactant present in a range of 0.1 to 5.0%; a stabilizer present in a range of 0.1 to 5.0%; a plasticizer present in a range of 0.1 to 5.0%, by weight of the total composition.

4. The novel, stable, synergistic nutritional composition according to claim 1, wherein the composition is useful for treating epilepsy, reflex epilepsy, epileptic seizures, nonepileptic seizures, provoked seizures, idiopathic generalized epilepsy, convulsion, absence seizures, atonic seizures, tonic seizures, clonic seizures, myoclonic seizures, febrile seizure, generalized seizures, focal seizures, absence seizures, temporal lobe seizures, atonic seizures, generalized tonic-clonic seizure, febrile seizures occipital lobe seizures, parietal lobe seizures, frontal lobe epilepsy, temporal lobe epilepsy, nocturnal epilepsy, neocortical epilepsy, infantile spasms hypothalamic hamartoma, fibrotic disorder, kidney diseases associated with nephrectomy, renal fibrosis, glomerular sclerosis and end stage renal disease, diabetic nephropathy, renal failure progression associated with hypertension, infarct, tumor, diabetes mellitus, autoimmunity, alcoholic fatty liver disease (ALFD) and insulin regulation.

5. A stable, orally active anti-seizure nutritional composition comprising: a synergistic combination of a therapeutically effective amount of tridecanoin and L-ergothioneine, wherein the tridecanoin and the L-ergothioneine are present in a weight ratio of 1:0.002 to 1:0.2 along with pharmaceutically acceptable excipients.

6. The stable, orally active anti-seizure nutritional composition according to claim 5, wherein the pharmaceutically acceptable excipients are selected from a group consisting of a diluent present in a range of 1 to 25%; a binder present in a range of 0.1 to 20%; a lubricant present in a range of 0.1 to 5.0%; a glidant present in a range of 0.1 to 5.0%; an additive present in a range of 1 to 5%; a surfactant present in a range of 0.1 to 5.0%; a stabilizer present in a range of 0.1 to 5.0%; a plasticizer present in a range of 0.1 to 5.0% by weight of the total composition.

* * * * *